United States Patent [19]

Murtiashaw et al.

[11] Patent Number: 5,336,771
[45] Date of Patent: * Aug. 9, 1994

[54] CERTAIN 3,4-DIHYDRO-2H-PYRANO[2,3-B]PYRIDINES

[75] Inventors: Charles W. Murtiashaw; George J. Quallich, both of North Stonington, Conn.

[73] Assignee: Pfizer Inc., New York, N.Y.

[*] Notice: The portion of the term of this patent subsequent to Nov. 26, 2008 has been disclaimed.

[21] Appl. No.: 961,049

[22] Filed: Oct. 14, 1992

Related U.S. Application Data

[60] Continuation of Ser. No. 750,787, Aug. 27, 1991, abandoned, which is a division of Ser. No. 490,906, Mar. 7, 1990, Pat. No. 5,068,333.

[51] Int. Cl.$^5$ ............... C07D 491/052; C07D 491/04
[52] U.S. Cl. ............................... 546/116; 546/14; 546/15; 546/303
[58] Field of Search ........................................ 546/116

[56] References Cited

U.S. PATENT DOCUMENTS 4,980,357 12/1990 Goldstein et al. ............ 514/278

FOREIGN PATENT DOCUMENTS

| 0040176 | 11/1981 | European Pat. Off. | 546/345 |
| 0097014 | 12/1983 | European Pat. Off. | 546/276 |
| 0136593 | 4/1985 | European Pat. Off. | 546/302 |
| 0306251 | 3/1989 | European Pat. Off. | 546/15 |
| 0014079 | 8/1990 | European Pat. Off. | 546/15 |
| 2455046 | 11/1980 | France | 548/301.1 |

OTHER PUBLICATIONS

March, Advanced Organic Chemistry, Second Edition, pp. 98–113, McGraw-Hill Publishes, 1979.
Chemical Abstracts, vol. 67, No. 15, Oct. 9, 1967, Columbus, Ohio, USA, H. Sliwa: "Synthesis of New Heterocylic Compounds", p. 6926; ref. No. 73537Y & C. R. Acad. Sci., Paris, Ser. C 264 [23], 1893–5, [1967], abstract.
Chemical Abstracts, vol. 113, No. 3, Jul. 16, 1990. R. Sarges et al.: "Spiro Hydantoin Aldoso Reductase Inhibitors Derived from 8-aza-4-chromanones", p. 648; ref. No. 23773V & J. Med., 1990, 33[7], 1859–65 (abstract).

Primary Examiner—Alan L. Rotman
Attorney, Agent, or Firm—Peter C. Richardson; Paul H. Ginsburg; Philip C. Strassburger

[57] ABSTRACT

The present invention relates to processes and intermediates for the preparation of spiro-heteroazolones. The latter compounds are useful as aldose reductase inhibitors.

4 Claims, No Drawings

CERTAIN 3,4-DIHYDRO-2H-PYRANO[2,3-B]PYRIDINES

This is a continuation of application Ser. No. 07/750,787, filed on Aug. 27, 1991, now abandoned, which is a divisional of U.S. Ser. No. 07/490,906 filed on Mar. 7, 1990, now U.S. Pat. No. 5,068,333.

BACKGROUND OF THE INVENTION

The present invention relates to processes and intermediates for the preparation of spiro-heteroazolones. The latter compounds are useful as aldose reductase inhibitors.

Spiro-heteroazolones that may be prepared by the processes disclosed herein are disclosed in European Patent Application No. 88307985.7, assigned to Pfizer Inc.

SUMMARY OF THE INVENTION

The present invention relates to a compound of the formula

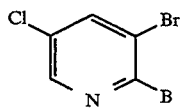

wherein B is hydroxide, chloro or bromo.

The present invention also relates to a compound of the formula

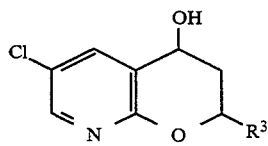

wherein $R^3$ is hydrogen or $(C_1-C_4)$alkyl

The present invention also relates to a compound of the formula

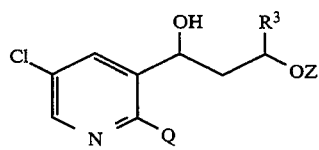

wherein $R^3$ is $(C_1-C_4)$ alkyl; Q is chlorine, bromine, or fluorine or OX, wherein X is $SO_2R^4$ and $R^4$ is $(C_1-C_4)$alkyl, trifluoromethyl or phenyl optionally substituted with 1 to 3 substituents independently selected from $(C_1-C_4)$alkyl, chloro and nitro; and Z is a negative charge, hydrogen, or an oxygen protecting group (e.g., a silyl-containing group such as t-butyldimethylsilyl).

The present invention also relates to a pure enantiomer of a compound of the formula

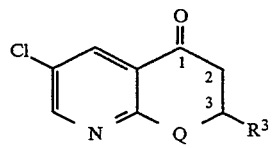

wherein $R^3$ is $(C_1-C_4)$ alkyl.

The present invention also relates to a compound of the formula:

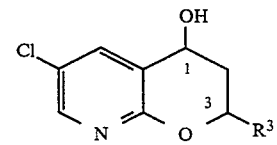

wherein $R^3$ is methyl and wherein the stereochemistry of the carbon at position 3 is pure in an absolute sense and may be of either the R or S configuration.

The present invention also relates to a process for preparing a compound of the formula

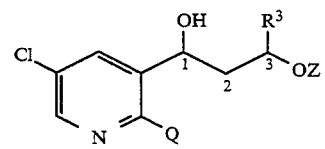

wherein Q and $R^3$ are as defined above and Z is an oxygen protecting group, comprising reacting a compound of the formula

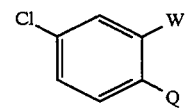

wherein W is bromo or iodo, and Q is as defined above, with lithium metal or an alkyl lithium reagent.

The present invention also relates to a process for preparing a compound of the formula

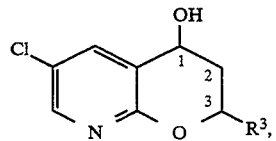

wherein the sterochemistry at the carbon labelled "3" is either pure in an absolute sense or a 1:1 mixture of R and S forms, and wherein $R^3$ is hydrogen or $(C_1-C_4)$alkyl, comprising reacting a compound of the formula

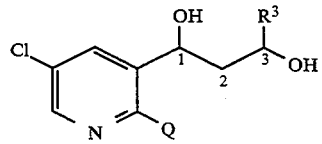

having the same stereochemistry at the carbon labeled "3" as the desired compound of formula VII, and wherein $R^3$ is defined as above and Q is chloro, bromo, fluoro or OX, wherein X is $SO_2R^4$ and $R^4$ is $(C_1-C_4)$alkyl, trifluoromethyl, or phenyl optionally substituted with 1 to 3 substituents independently selected from $(C_1-C_4)$alkyl, chloro and nitro, with a base. Suitable bases include sodium hydride, potassium hydride, lithium diisopropyl amide, lithium hexamethyldisilazide, potassium hexamethyldisilazide, and other non-nucleophilic bases.

The present invention also relates to a process for preparing a pure enantiomer or a racemic mixture of a compound of the formula

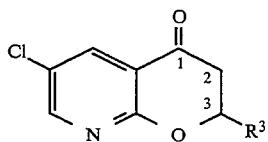   VIII wherein $R^3$ is as defined above, comprising reacting a compound of the formula VII above, having the same stereochemistry at the carbon labeled "3" as the desired compound of formula VIII, with a suitable oxidizing reagent such as pyridinium chlorochromate, Jones reagent or manganese dioxide.

The present invention also relates to a process for preparing a pure enantiomer of a compound of the formula

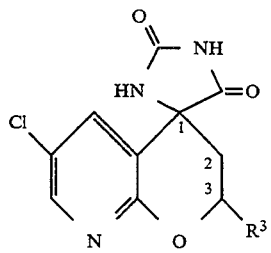   IX wherein $R^3$ is as defined above, comprising:
a) reacting a compound of the formula

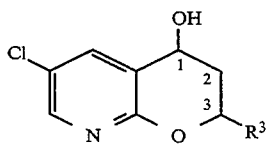   VII having the same absolute stereochemistry at the carbon labelled "3" as the desired compound of formula IX and wherein $R^3$ is as defined above, with a suitable oxidizing reagent such as pyridinium chlorochromate, Jones reagent or manganese dioxide, to form a pure enantiomer of a compound of the formula

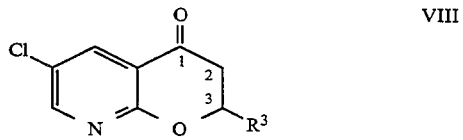   VIII having the same absolute stereochemistry at the carbon labelled "3" as the desired compound of formula IX, and (b) condensing said compound of formula VIII with an alkali metal cyanide (e.g. sodium cyanide or potassium cyanide) and ammonium carbonate.

DETAILED DESCRIPTION OF THE INVENTION

The following reaction scheme illustrates the novel processes and the preparation of the novel intermediates of the present invention. It also illustrates the method by which such processes and intermediates can be used to prepare the spiroheteroazolones disclosed in European Patent Application No. 88307985.7.

The novel compounds of this invention are included in the generic formulas designated II, IV, V, VII and VIII in the reaction scheme. The novel processes of this invention are represented by steps C, E and F of the reaction scheme.

Except where otherwise noted, $R^3 R^4$, W, X, Z, and Q in the reaction scheme and discussion that follow are defined as above.

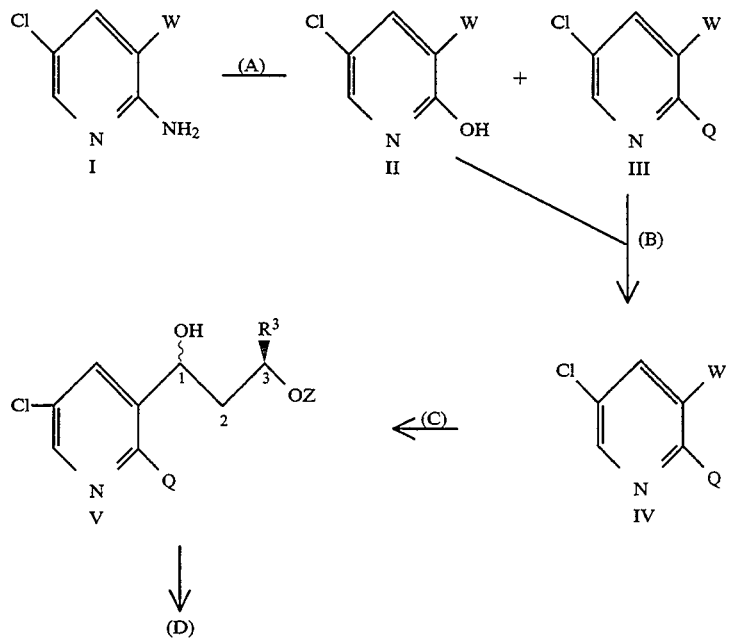

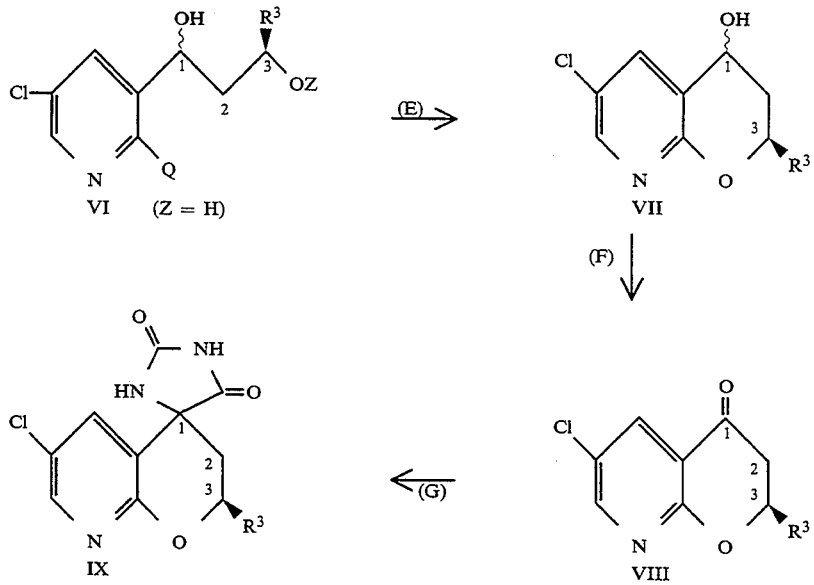

The first step (A) in the sequence involves reacting the appropriate compound of formula I, wherein W is bromo or iodo, with water in the presence of a suitable diazotizing reagent to produce compounds of the formulae II and III, wherein W is bromo or iodo. Examples of such reagents are t-butyl nitrite, sulfuric acid/sodium nitrite and hydrochloric acid/sodium nitrite. The preferred diazotizing agent is hydrochloric acid/sodium nitrite. This step is generally carried out at a temperature from about $-10°$ C. to about $50°$ C, preferably at about $0°$ C.

The compounds of formulae II and III are then reacted in step (B) with a suitable chlorinating or brominating reagent in the presence of an appropriate polar aprotic reaction inert solvent. Suitable chlorinating reagents are $POCl_3$, $PCl_3$ and $PCl_5$. $POCl_3$ is preferred. Suitable brominating agents are $POBr_3$ and $PBr_3$. $POBr_3$ is preferred. Suitable solvents include dimethylformamide, dimethylacetamide and N-methylpyrrolidinone, with dimethylformamide being preferred. Generally, this step is carried out at a temperature from about $0°$ C. to about $100°$ C., with about $70°$ C. being preferred. Step (B) produces a compound of the formula IV, wherein W is bromo or iodo.

The compound of formula IV so formed is then treated in Step (C) with lithium metal or an alkyl lithium reagent, in the presence of an aprotic non-polar reaction inert solvent, to form a 3-lithiated pyridine. Suitable alkyl moieties of the alkyl lithium include $(C_1-C_6)$alkyl. In preferred embodiments of the present invention, respectively, the alkyl moiety of the alkyl lithium is n-butyl. This reaction is typically carried out at a temperature from about $-100°$ C. to about $-20°$ C. The preferred temperature is $-78°$ C.

Suitable solvents include di-isopropyl ether, di-ethyl ether and tetrahydrofuran, with di-isopropyl ether and di-ethyl ether being preferred. A compound of the formula

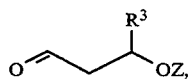

wherein Z is a negative change or an oxygen protecting group, is then added to the 3-lithiated pyridine to produce a compound of the formula V, wherein Z a negative charge or an oxygen protecting group. Examples of suitable oxygen protecting groups include trisubstituted silyl (e.g., t-butyldimethylsilyl), tetrahydropyranyl, methoxyethoxymethyl, ethoxyethyl, methoxymethyl and benzyl. Step (C) is generally carried out at temperatures from about $-100°$ C. with about $-20°$ C., with about $-78°$ C. being preferred.

The carbon to which $R^3$ is attached in the compound having the formula

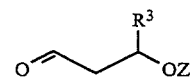

is a chiral center. The compound of formula V formed in step (C) will have the same absolute stereochemistry at this chiral center as the aldehyde from which it was formed. As shown in the reaction scheme, this stereochemistry will be retained through the entire reaction sequence in the compounds having formulae VI, VII, VIII and IX. Therefore, either racemic mixtures or the pure enantiomers of compounds VIII and IX may be prepared by the method illustrated in the reaction scheme and described herein, depending upon stereochemistry of the aldehyde used in step (C).

The compound of formula V, wherein Z is an oxygen protecting group, is then reacted in step (D) with a suitable desilylating agent in the presence of a reaction inert solvent to form a compound of the formula V, wherein Z is hydrogen (also designated as formula VI in the reaction scheme). Suitable desilylating agents include tetra-n-butyl ammonium fluoride, hydrofluoric acid and cesium fluoride. The preferred desilylating agent is tetra-n-butyl ammnonium fluoride. Examples of suitable solvents are acetonitrile, methanol and tetrahydrofuran, with tetrahydrofuran being preferred. Step (D) is typically carried out at temperatures from about $-20°$ C. to about $50°$ C, with about $-5°$ C. being preferred.

Compounds of the formula V, wherein Z is a negative charge, may be prepared by deprotonating the corresponding compounds of the formula V, wherein Z is hydrogen (i.e., compounds of the formula VI) with an appropriate base. Examples of appropriate bases are sodium. hydride, potassium hydride, lithium diisopropylamide, lithium hexamethyldisilylazide, and potassium hexamethyldisilylazide. Examples of appropriate solvents for this reaction are tetrahydrofuran, dimethylformamide, isopropyl ether and diethyl ether.

The compound of formula VI, wherein Z is hydrogen, is then treated in Step (E) with a suitable base in the presence of a reaction inert polar solvent, to form a compound of the formula VII. Suitable solvents include dimethylformamide, dimethylsulfoxide and ($C_1$–$C_4$)alcohols. Tert-butanol is preferred. Suitable bases include potassium t-butoxide, NaH, n-butyl-lithium, 1,8-diazabicyclo[5.4.0]undec-7-ene, sodium hydroxide, 1,5-diazabicyclo[4.3.0]non-5-ene and potassium hexamethyldisilazide. Potassium t-butoxide is preferred. Step (E) is typically carried out at a temperatures from about 0° C. to about 100° C., preferably at about 83° C.

The compound of formula VII is then reacted in Step (F) with a suitable oxidizing reagent (e.g., pyridinium chlorochromate, Jones reagent or manganese dioxide) in the presence of a reaction inert solvent (e.g., $CH_2Cl_2$, acetone or toluene) to yield a compound of the formula VIII. This reaction is generally performed at temperatures from about −10° C. to about 100° C., with about 25° C. being preferred.

The compounds of the Formula VIII so formed may be condensed with an alkali metal cyanide (e.g. sodium cyanide or potassium cyanide) and ammonium carbonate to form a spiro-imidazolidinedione product having the formula IX. This reaction, illustrated in step (G), is typically carried out in the presence of a reaction-inert polar organic solvent. Appropriate solvents include cyclic ethers such as dioxane and tetrahydrofuran, lower alkylene glycols like ethylene glycol, water miscible lower alkanols such as methanol, as well as N,N-di(lower alkyl) lower alkanoamides such as N,N-dimethylacetamide. In general, this reaction is conducted at temperatures from about 25° C. to about 150° C. Upon completion of the reaction, the desired product is isolated in a conventional manner, by dilution with ice water and acidification. Further purification can be carried out by silica gel column chromatography.

The spiro-imidazolidinedione compounds of formula IX are aldose reductase inhibitors and are useful in lowering sorbitol levels in the sciatic nerve, retina and lens of diabetic subjects. Examples of such compounds are (+) -cis-6'-chloro-2', 3'-dihydro-2'-methyl-spiro-[imidazolidine-4,4'-4'H-pyrano-2,3-b]pyridine]-2,5-dione (where cis means that 2'-methyl and 4'-NH are on the same side of the pyran ring), (+) -trans-6'-chloro-2', 3'-dihydro-2'-methylspiro-[imidazolidine-4,4'-4'H-pyrano[2,3-b]-pyridine]-2,5-dione (where trans means that 2'-methyl and 4'-NH are on opposite sides of the pyran ring), (+)-cis-6'-fluoro-2', 3'-dihydro-2'-methyl-spiro- [imidazolidine-4,4'-4'H-pyrano[2,3-b]pyridine]-2,5-dione, (+)-cis6'-bromo-2', 3'-dihydro-2'-methyl-spiro- [imidazolidine-4,4'-4'H-pyrano[2,3-b]pyridine]-2,5-dione, (4'S) (2'R) -6'-chloro-2', 3'-dihydro-2'-methyl-spiro- [imidazolidine-4,4'-4'H-pyrano [2,3-b]-pyridine]-2,5-dione and (4'S) (2'R)-6'-chloro-2', 3'-dihydro-2'-methyl-spiro[imidazolidine-4,4'-4'H-pyrano-[2,3-b]pyridine]-2,5-dione-8'-oxide.

Unless indicated otherwise, the pressures of the foregoing reactions are not critical. Generally, the reaction pressures will be about 0.5 to about 3 atmospheres, preferably ambient pressure ( i.e., about one atmosphere).

The following Examples are illustrative of the compounds and processes of the present invention. All melting points are uncorrected.

EXAMPLE 1

2-Amino-3-bromo-5-chloropyridine

An acetic acid (400 mL) suspension of sodium acetate (57.1 g, 0.696 mol) and 2-amino-5-chloropyridine (89.5 g, 0.696 mol) was treated with a solution of bromine (35.9 mL, 0.696 mol) in acetic acid (15 mL) over a period of 1.25 hours with gentle warming to 43° C. The resulting orange slurry was then cooled to 15° C. and filtered to provide a solid which was subsequently dissolved in water, basified (pH 8.5 ) with 1N NaOH, and extracted with ethyl acetate (5×150 mL). The combined organic layers were washed with 10% sodium bisulfite (2×150 mL), dried over magnesium sulfate, and condensed to give 102.1 g (70.7%) of a yellow solid, m.p. 83°–85° C.: IR($CHCl_3$) 3683, 3504, 3401, 2987, 2482, 2392, 1608, 1571, 1544, 1455, 1389, 1316, 1207, 1127, 1057, 1026, 895, 881, 650, 607, 249, 236cm ; H NMR (300MHz, $CDCl_3$)δ 5.20 (br s, 2H), 7.70 (d, 1H), J=2.2Hz), 8.0 (d, 1H, J=2.2 Hz); $^{13}$C NMR ($CDCl_3$)δ 104.08, 120.33, 139.62, 145.24, 154.10; exact mass calculated for $C_5H_4N_2BrCl$=205.9246. High resolution mass spec. 205. 9246.

EXAMPLE 2

3-Bromo-5-Chloropyridin-2-One

To a cooled (0° C.) solution of 2-amino-3-bromo-5-chloropyridine (100 g, 0.482 tool) in water (815 mL) and concentrated HCl (130 mL) was added a solution of sodium nitrite (33.26 g, 0.482 tool) in water (272 mL). The resulting suspension was allowed to warm to room temperature and stir for 18 hours, at which point the solids were filtered, washed with carbon tetrachloride (2×50 mL), and dried in a vacuum oven (40° C.) to yield 75.1 g (74.8%) of gray-yellow so lid, m.p. 170°–173° C.: IR (mineral oil (Nujol (trademark)) 3111, 3041, 2947, 2850, 2722, 1814, 1696, 1663,1743, 1585, 1527, 1462, 1377, 1302, 1234, 1171, 1153, 1123, 1106, 1040, 917, 896, 876, 839, 747, 726, 644, 635, 561, 539, 523, 410, 251, 235, 225, 220cm$^{-1}$; $^1$H NMR (300 MHz, $D_6$-DMSO)δ 7.72 (d, 1H, J=2.2Hz) , 8.08 (d, 1H , J=2 . 2Hz ), 12.41 (br s, 1H); $^{13}$C NMR (DMSO) δ 110.88, 115.35, 134.08, 142.64, 157.56; exact mass calculated for $C_5H_3NBrClO$=206.9086. High resolution mass spec. 206.9093.

EXAMPLE 3

3-Bromo-2,5-Dichloropyridine

To a solution of 3-bromo-5-chloropyridin-2-one (84.3 g, 0.404 tool) in DMF (100 mL) was added $POCl_3$ (56.5 mL, 0.61 tool) via dropping funnel over 3 hours at room temperature. The resulting black solution was then heated to 70° C. and allowed to stir for 3 days. After cooling to room temperature, the solution was poured into 1L of ice/water, filtered, and the solid dried in a vacuum oven to provide 81.76 g (89%) of the desired 3-bromo-2, 5-dichloropyridine as an off-white solid, m.p. 39°–41° C.: IR($CHCl_3$) 3867, 3663, 2989, 2734, 1812, 1606, 1547, 1400, 1366, 1230, 1155, 1129, 1074, 1027, 894, 658, 563cm ; HNMR (300 MHz, CDCl$_3$)δ 8.0 (d, 1H, J=2.2Hz) , 8.35 (d, 1H, J=2.2Hz); $^{13}$C NMR (CDCl$_3$)δ 120.43, 130.74, 141.46, 146.64, 148.99; exact mass calculated for C$_5$H$_2$NBrCl$_2$=224.8748; high resolution mass spec. 224.8764.

EXAMPLE 4

3- [3(R)-t-Butyldimethylsiloxy, 1-Hydroxybutyl]-2,5-Dichloropyridine

To a cooled (−70° C.) solution of n-butyllithium (129.3 mL of 1.18M hexanes solution, 0.153 mol) in isopropyl ether was added a solution of 3-bromo-2,5-dichloropyridine (36.45 g, 0,161 mol) in isopropyl ether (225 mL) over a period of 30 minutes. The resulting white suspension was then treated with a solution of 3 (R) -t-butyldimethylsiloxybutyraldehyde (34.14 g, 0,169 tool) in isopropyl ether (106 mL) and allowed to stir for an additional 30 minutes at −70° C. followed by warming to room temperature. After the addition of 480 mL of water, the biphasic mixture was separated and the organic layer was extracted with isopropyl ether (2×200 mL). The combined organic layers were washed once with water, heated with decolorizing carbon [G-60 DARCO (trademark)] filtered through diatomateous earth [Celite (trademark)] and condensed on a rotary evaporator. The resulting hazy yellow liquid was heated at 80° C. under high vacuum overnight to yield the desired product (mixture of diastereomers) as an amber oil (40.52 g, 72%): R$_f$ 0.36 (25% Et$_2$O in hexanes); $^1$H NMR (60 MHz, CDCl$_3$)δ 0.1 (s, 6H), 0.82 (s, 9H) , 1.18 (m, 3H) , 1.72 (m, 2H) , 4.16 (m, 1H) , 4.42 (m, 1H) , 5.10 (m, 1H) , 7.92 (d, 1H, J=2.6 Hz) , 8.13 (d, 1H, J=2.6 Hz) .

EXAMPLE 5

2,5-Dichloro-3-[3(R)-Hydroxy-1-Hydroxy1-Butyl]-Pyridine

To a cooled (5° C.) THF (tetrahydrofuran) (161.5 mL) solution of the title compound of Example 4 (40.38 g, 0.115 mmol) was added 115.3 mL of a 0.1M solution of tetrabutylammonium fluoride in THF. Following warming to room temperature and stirring for 2.5 hours, the clear dark solution was condensed on a rotary evaporator and then reduced further under high vacuum. After the resulting oil was dissolved in water and extracted with Et$_2$O (ethyl ether) (2×150 mL), the combined organic extracts were washed once with water, concentrated to an oil, and chromatographed (70–230 mesh silica gel, 10% Et$_2$O in CH$_2$Cl$_2$) to provide the product as a semi-solid (16.8 g, 61.7%) mixture of diastereomers): R$_f$ 0.35 and 0.22 (25% Et$_2$O in CH$_2$Cl$_2$); $^1$H NMR (250 MHz, CDCl$_3$)δ 1.30 (m, 6H) , 1.53 (m, 2H), 1.96 (m, 2H), 2.42 (m, 1H), 2.73 (m, 1H), 4.10 (m, 1H), 4.28 (m, 1H), 4.30 (s, 1H), 4.63 (d, 1H, J=4.5 Hz), 5.18 (m, 1H), 5.31 (m, 1H), 8.02 (d, 1H, J=2.6 Hz), 8.24 (m, 1H).

EXAMPLE 6

6-Chloro-3,4-Dihydro-4-Hydroxy-2 (R) -Methyl-2H) -Pyrano[2, 3-b]Pyridine

To a mixture of the title compound of Example 5 (16.4 g, 0.069 tool) and tert-butyl alcohol (115 mL) was added 23.39 g (0.208 mol) of potassium t-butoxide. After heating at reflux for 3 hours, the reaction was concentrated, diluted with water (150 mL) and extracted with isopropyl ether (3×150 mL). The combined extracts were washed with water, dried over MgSO$_4$ and concentrated to a clear oil which was chromatographed (70–230 silica gel, CH$_2$Cl$_2$ as eluent) to yield 10.8 g (78%) of the desired product as a mixture of diastereomers: R$_f$ 0.39 (25% Et$_2$O in CH$_2$Cl$_2$); $^1$H NMR (250 MHz, CDCl$_3$) 1.47 (d, 3H, J=6.3 Hz), 1.49 (d, 3H, J=6.3 Hz), 1.78 (m, 2H), 2.08 (m, 2H), 3.02 (d, 1H, J=4.5 Hz), 3.15 (d, 1H, J=7.7Hz), 4.39 (m, 1H), 4.58 (m, 1H), 4.80 (m, 1H), 4.93 (m, 1H), 7.64 (d, 1H, J=2.6 Hz), 7.83 (d, 1H, J=2.6 Hz), 8.00 (d, 1H, J=2.6 Hz), 8.08 (d, 1H, J=2.6 Hz).

EXAMPLE 7

6-Chloro-3,4-Dihydro-2 (R) -Methyl-4-Oxo-2H-Pyrano[2,3-b]Pyridine

To a suspension of the title compound of Example 6 (10.56 g, 0. 0529 tool) and diatomaceous earth [Celite (trademark)](14.25 g) in CH$_2$Cl$_2$ (106 mL) was added pyridinium chlorochromate (28.51 g, 0,132 mol) at room temperature. After stirring for two hours, the reaction mixture was filtered through a pad of silica gel (100 g, 230–400 mesh) and condensed on a rotary evaporator. The crude white solid was recrystallized from isopropyl ether to yield 8.15 g (78%) of the pure azachromanone, m.p. 85°–87° C.: []D=+73.8° (c=1.0, methanol), R$_f$ 0.28 (50% Et$_2$O in hexanes); $^1$H NMR (250 MHz, CDCl$_3$) 1.55 (d, 3H, J=7.0 Hz) , 2.67 (m, 2H) , 4.67 (m, 1H) , 8.08 (d, 1H, J=2.6 Hz) , 8.32 (d, 1H, J=2.6 Hz); Mass spec. 197 (M+); Anal. Calculated for C$_9$H$_8$ClNO$_2$: C, 54.70; H, 4.08. Found: C, 54.74; H, 4.13.

EXAMPLE 8

2 , 3-Dibromo-5-Chloropyridine

3-Bromo-5-chloropyridone (8.0 g, 38.4 mmole) was dissolved in dimethylformamide (60 ml) at ambient temperature. Phosphorus (V) tribromide oxide (16.5 g, 57.6 mmoles) was added and the reaction heated to 80° C. for 72 hours. After cooling, the reaction was poured onto 800 g of ice. Vacuum filtration provided the product as a dark solid (6.85 g). Hexane (225 ml) and decolorizing carbon was added to the crude product and the contents heated to reflux and then filtered through celite. The clear colorless filtrate was stripped under vacuum to yield the product as a white solid 1H NMR (250 MHz , CDC13) (5.3 g, 51%) m.p. 39.5–43° C. $^1$H NMR (250 MHz, CDCl$_3$) $^1$H 8.28 (d, J=2 Hz), 7.89 (d, J=2 Hz); $^{13}$C NMR (CDCl$_3$) 146.93, 141.45, 141.02, 131.34, 124.01; Anal. Calculated for C$_5$H$_2$Br$_2$ClN: C, 22.13; H, 0.74; N, 5.16. Found C, 21.93; H, 0.53; N, 4.90. IR (neat) 3060, 1538, 1405, 1370, 1135, 1030, 905 cm ; Mass spec., (relative intensity) 269 (M+, 68), 190 (100), 111 (83).

We claim:

1. A compound of the formula having the S configuration

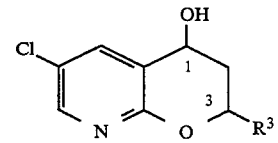

wherein R$^3$ is (C$_1$-C$_4$) alkyl.

2. A compound according to claim 1, wherein R$^3$ is methyl.

3. A compound according to claim 2, wherein the stereochemistry of the carbon at position 3 is pure in an absolute sense and is the configuration.
4. A pure enantiomer of a compound of the formula
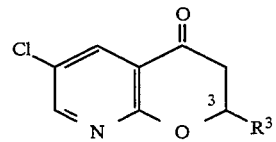
wherein $R^3$ is $(C_1-C_4)$alkyl.
* * * * *